(12) United States Patent
Kawabata et al.

(10) Patent No.: US 11,412,945 B2
(45) Date of Patent: Aug. 16, 2022

(54) MUSCLE ACTIVITY MEASUREMENT DEVICE AND MUSCLE ACTIVITY MEASUREMENT METHOD

(71) Applicants: National University Corporation Tokyo Medical and Dental University, Tokyo (JP); TDK CORPORATION, Tokyo (JP)

(72) Inventors: Shigenori Kawabata, Tokyo (JP); Shuichi Okawa, Tokyo (JP); Shuta Ushio, Tokyo (JP)

(73) Assignees: National University Corporation Tokyo Medical and Dental University, Tokyo (JP); TDK CORPORATION, Tokyo (JP)

( * ) Notice: Subject to any disclaimer, the term of this patent is extended or adjusted under 35 U.S.C. 154(b) by 499 days.

(21) Appl. No.: 16/307,192

(22) PCT Filed: Jun. 6, 2017

(86) PCT No.: PCT/JP2017/020955
§ 371 (c)(1),
(2) Date: Dec. 5, 2018

(87) PCT Pub. No.: WO2017/213127
PCT Pub. Date: Dec. 14, 2017

(65) Prior Publication Data
US 2019/0125205 A1 May 2, 2019

(30) Foreign Application Priority Data
Jun. 8, 2016 (JP) .............................. JP2016-114482

(51) Int. Cl.
*A61B 5/05* (2021.01)
*A61B 5/00* (2006.01)
(Continued)

(52) U.S. Cl.
CPC ............ *A61B 5/05* (2013.01); *A61B 5/02438* (2013.01); *A61B 5/02444* (2013.01);
(Continued)

(58) Field of Classification Search
CPC ......... A61B 5/05; A61B 5/242; A61B 5/4519; A61B 5/02438; A61B 5/02444; A61B 2562/0223; A61B 5/065
See application file for complete search history.

(56) References Cited

U.S. PATENT DOCUMENTS 7,922,773 B1 * 4/2011 Kuiken .................... A61F 2/60
623/24
2007/0167850 A1 7/2007 Russell et al.
(Continued)

FOREIGN PATENT DOCUMENTS

JP   H07-181239 A   7/1995
JP   2007-520273 A  7/2007
(Continued)

OTHER PUBLICATIONS

Notification of Reasons for Refusal in counterpart Japanese Patent Application No. 2018-522502 dated Oct. 6, 2020 (5 pages).
(Continued)

*Primary Examiner* — Bill Thomson
*Assistant Examiner* — Zainab Mohammed Aldarraji
(74) *Attorney, Agent, or Firm* — Osha Bergman Watanabe & Burton LLP (57) ABSTRACT

The present invention addresses the problem of providing a muscle activity measurement device and a muscle activity measurement method which make it possible to measure the muscle activity of an object to be sensed with increased accuracy. The muscle activity measurement device is provided with a magnetic sensor unit which senses a magnetic field generated from a living body. The muscle activity
(Continued)

measurement device identifies an installed direction of the muscle activity measurement device, and includes an indication, on a surface of a container, which comprises identification information for installing the muscle activity measurement device in such a way that a magnetism sensing direction X of the magnetic sensor unit and the direction in which the muscle fibers of the living body as the object to be sensed extend are substantially orthogonal to each other.

7 Claims, 9 Drawing Sheets

(51) Int. Cl.
    *A61B 5/242*     (2021.01)
    *A61B 5/024*     (2006.01)
    *A61B 5/06*     (2006.01)

(52) U.S. Cl.
    CPC ............ *A61B 5/242* (2021.01); *A61B 5/4519* (2013.01); *A61B 5/065* (2013.01); *A61B 2562/0223* (2013.01)

(56) References Cited

U.S. PATENT DOCUMENTS

| | | |
|---|---|---|
| 2012/0330124 A1 | 12/2012 | Fukuda et al. |
| 2015/0366504 A1* | 12/2015 | Connor ................ A61B 5/6804 600/301 |

FOREIGN PATENT DOCUMENTS

| | | | |
|---|---|---|---|
| JP | 2010-051682 A | 3/2010 | |
| JP | 2010051682 A * | 3/2010 | |
| JP | 2011-255051 A | 12/2011 | |
| JP | 5433474 B2 | 3/2014 | |
| JP | 201649170 A | 4/2016 | |
| JP | 2016049170 A * | 4/2016 | |
| WO | 2015013552 A1 | 1/2015 | |
| WO | WO-2015013552 A1 * | 1/2015 | ........... A61B 5/7225 |

OTHER PUBLICATIONS

Office Action issued in Japanese Application No. 2018-522502; dated Dec. 15, 2020 (5 pages).

Extended European Search Report issued in European Application No. 17810302.4, dated Oct. 4, 2019 (9 pages).

International Search Report issued in PCT/JP2017/020955 dated Aug. 29, 2017 (2 pages).

Written Opinion of the International Searching Authority issued in PCT/JP2017/020955 dated Aug. 29, 2017 (4 pages).

Hamada, N., "Development of Low Noise MI Sensor and Its Applications", PIERS Proceedings, 2014, pp. 860-862 (3 pages).

Mantel, Norm P., "Design Optimization of a Transducer for Magnetomyography", Annual International Conference of the IEEE Engineering Medicine and Biology Society, 1991, vol. 13, No. 4, pp. 1709-1710 (2 pages).

Uchiyama, Tsuyoshi, "Measurement of Spontaneous Oscillatory Mangetic Field of Guinea-Pig Smooth Muscle Preparation Using Pico-Tesla Resolution Amorphous Wire Magneto-Impedance Sensor", IEEE Transactions on Mangetics, 2011, vol. 47, No. 10, pp. 3070-3073 (4 pages).

* cited by examiner

MUSCLE ACTIVITY MEASUREMENT DEVICE AND MUSCLE ACTIVITY MEASUREMENT METHOD

TECHNICAL FIELD

The present invention relates to a muscle activity measurement device and a muscle activity measurement method which use a magnetic sensor.

BACKGROUND ART

For spinal and spinal cord diseases, an operation is performed if conservative treatment such as pharmacotherapy and physical therapy do not achieve the expected effects. In order to prevent complications after surgery such as spinal cord disorders and nerve disorders, the patient's spinal cord function and nerve function is monitored during surgery. This monitoring involves applying electrical stimuli to the patient's nerves and checking if muscle activity in various parts of the body is responding correctly to the electrical stimuli.

The above-mentioned monitoring is generally performed by directly attaching a plurality of bioelectrodes to a patient's skin, hooking wires to each of the bioelectrodes and using the bioelectrodes to measure action potential generated from muscle fibers. However, directly attaching electrodes to a patient's skin puts the patient at risk of contracting an infectious disease from bacteria in the operating field.

In order to help overcome this problem, Patent Document 1 discloses a muscle activity measurement device that includes a magnetic field fluctuation measurement member formed of a magnetic impedance element which has varying impedance according to a magnetic field generated based on muscle activity, which is the activity of a muscle group of a patient. The magnetic field fluctuation measurement member includes a magnetic field detection unit which detects a magnetic field. The magnetic field fluctuation measurement member measures magnetic field fluctuation, which is fluctuation of the detected magnetic field. The muscle activity measurement device also includes muscle activity measurement means configured to measure muscle activity of the subject on the basis of the magnetic field fluctuation measured by the magnetic field fluctuation measurement member. Measurement of the magnetic field generated due to muscle activity (hereinafter also referred to as "muscular magnetic field") does not require attaching sensors to a patient's skin as in electric potential measurement, which means that infectious diseases can be prevented.

Patent Document 1: Japanese Unexamined Patent Application, Publication No. 2010-051682

DISCLOSURE OF THE INVENTION

Problems to be Solved by the Invention

However, even with the muscle activity measurement device described in Patent Document 1, there is still room for improvement in terms of improving the accuracy of measuring magnetic field fluctuation.

It is an object of the present invention to provide a muscle activity measurement device and a muscle activity measurement method which can measure muscle activity to be detected more accurately.

Means for Solving the Problems

The inventors of the present invention conducted intensive study to solve the above-mentioned problem and found that a muscular magnetic field generated due to muscle activity occurs in a direction substantially perpendicular to muscle fibers. As a result, the inventors arrived at the present invention. More specifically, the present invention provides the following.

(1) The present invention is a muscle activity measurement device including a magnetic sensor unit configured to detect a magnetic field generated from a body; and identification means configured to identify a placement direction of the muscle activity measurement device, the identification means including identification information used for placing the muscle activity measurement device such that a sensing direction of the magnetic sensor unit is substantially orthogonal to an extension direction of muscle fibers in the body to be detected.

(2) The present invention is a muscle activity measurement device including a magnetic sensor unit configured to detect a magnetic field generated from a body; and identification means configured to identify a placement direction of the muscle activity measurement device, the identification means including identification information used for placing the muscle activity measurement device such that a sensing direction of the magnetic sensor unit substantially coincides with a direction of a muscular magnetic field generated due to muscle activity in the body to be detected.

(3) The present invention is the muscle activity measurement device of (1) or (2), further including a calculation unit configured to generate biomagnetic information on the basis of a signal detected by the magnetic sensor unit; a wireless module configured to wirelessly transmit the biomagnetic information generated by the calculation unit to an external device; and a power supply unit configured to supply electric power to the magnetic sensor unit, the calculation unit and the wireless module.

(4) The present invention is the muscle activity measurement device of (3), further including a substrate; and a container which houses the substrate, in which the magnetic sensor unit is mounted to one surface of the substrate, the calculation unit and the wireless module are mounted to another surface of the substrate, and the identification means is provided on a front surface of the container.

(5) The present invention is the muscle activity measurement device of (4) in which the identification means includes a display of the placement direction of the muscle activity measurement device on the front surface of the container.

(6) The present invention is the muscle activity measurement device according to (4) or (5) in which the identification means includes a shape of the container.

(7) The present invention is the muscle activity measurement device according to (6) in which the container has a rectangular shape or an elliptical shape.

(8) The present invention is the muscle activity measurement device according to (7) in which a transverse direction of the container substantially coincides with a sensing direction of the magnetic sensor unit.

(9) The present invention is a muscle activity measurement method of disposing the muscle activity measurement device of (1) on a body surface of the body with a sensing direction of the magnetic sensor unit substantially orthogonal to an extension direction of muscle fibers in the body to be detected.

Effects of the Invention

According to the present invention, there can be provided a muscle activity measurement device and a muscle activity measurement method which can measure muscle activity to be detected more accurately.

BRIEF DESCRIPTION OF THE DRAWINGS

FIG. 3 are diagrams for explaining the muscle activity measurement device according to the first embodiment when viewed from the front, in which

FIG. 4 are diagrams for explaining the muscle activity measurement device according to the first embodiment when viewed from the rear, in which

FIG. 6 are diagrams for explaining a muscle activity measurement device according to a second embodiment of the present invention when viewed from the front, in which

FIG. 7 are diagrams for explaining the muscle activity measurement device according to the second embodiment when viewed from the rear, in which

PREFERRED MODE FOR CARRYING OUT THE INVENTION

Specific embodiments of the present invention are described in detail below, but the present invention is not limited to the following embodiments and may be changed as appropriate without departing from the object of the present invention.

First Embodiment

Figure 1:
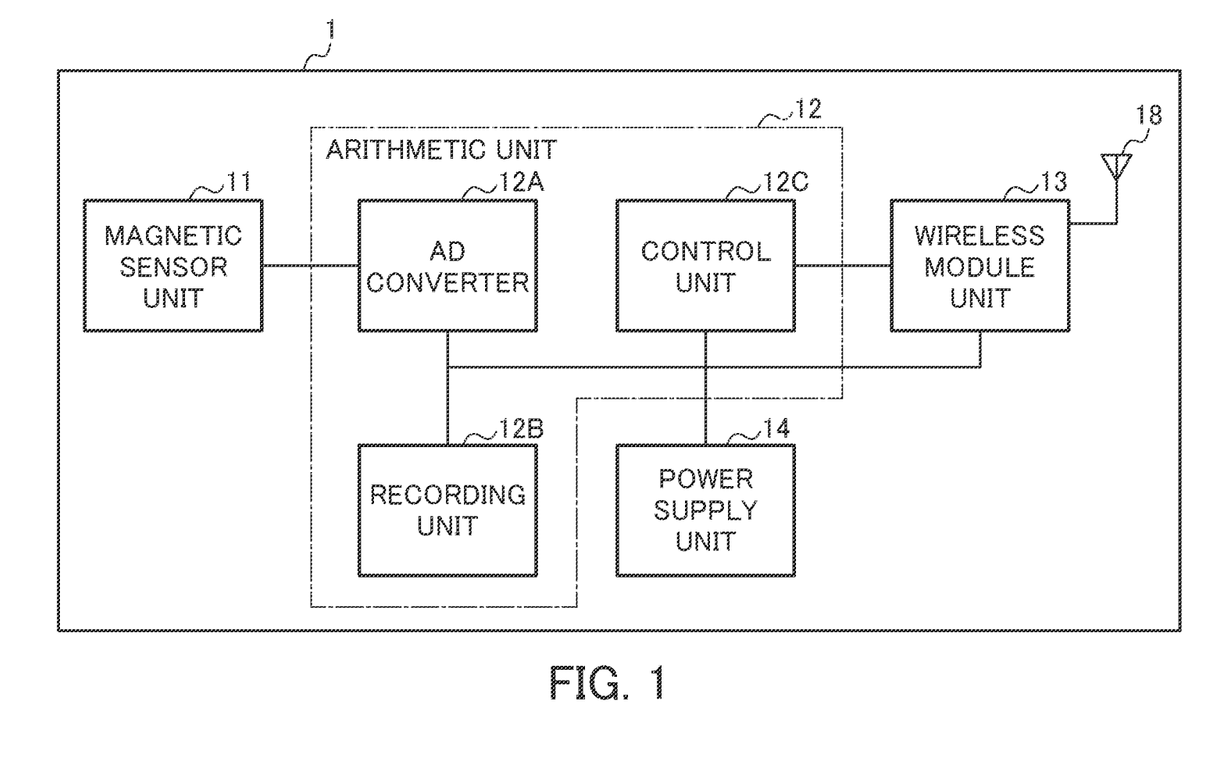
FIG. 1 is a block diagram for illustrating the configuration of a muscle activity measurement device according to a first embodiment of the present invention.

[Muscle Activity Measurement Device 1]
FIG. 1 is a block diagram for illustrating the configuration of a muscle activity measurement device 1 according to a first embodiment. As illustrated in FIG. 1, the muscle activity measurement device 1 according to this embodiment includes a magnetic sensor unit 11 configured to detect a magnetic field generated by a body, a calculation unit 12 configured to generate biomagnetic information on the basis of a signal detected by the magnetic sensor unit 11, a wireless module unit 13 configured to wirelessly transmit the biomagnetic information generated by the calculation unit 12 to an external device, and a power supply unit 14 configured to supply electric power to the calculation unit 12 and the wireless module unit 13.

[Magnetic Sensor Unit 11]
The magnetic sensor unit 11 is configured to detect a muscular magnetic field generated by a body. The type of magnetic sensor used for the magnetic sensor unit 11 is, for example, a giant magnetoresistance sensor (GMR sensor), a tunnel magneto resistance sensor (TMR sensor), an anisotropic magneto resistive sensor (AMR sensor), a magnetic impedance sensor (MI sensor) or a fluxgate sensor. The magnetic sensor used in this embodiment may be any magnetic sensor provided that the sensor can detect a magnetic field between $10^{-4}$ T (tesla) and $10^{-10}$ T (tesla).

Figure 2:
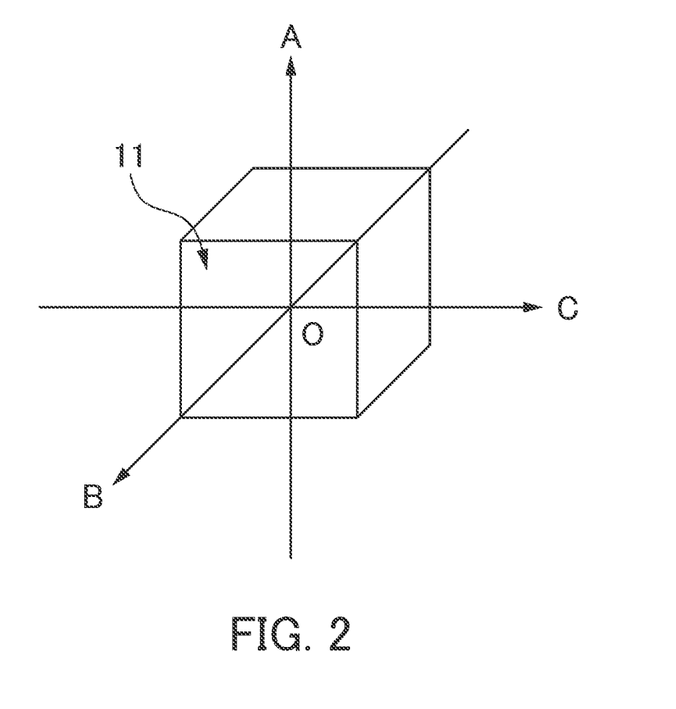
FIG. 2 is a schematic diagram for explaining a sensing direction of a magnetic sensor unit mounted to the muscle activity measurement device.

In this embodiment, the magnetic sensor used as the magnetic sensor unit 11 includes a direction in which sensitivity reaches a maximum, that is, a so-called sensing direction. For example, as illustrated in FIG. 2, the "sensing direction" is a direction in which, when sensitivity of a magnetic field in an A-direction of the magnetic sensor unit 11 is defined as $S_A$, sensitivity of magnetism in a B-direction is defined as $S_B$, and sensitivity of magnetism in a C-direction is defined as $S_C$, the sensitivities $S_A$, $S_B$ and $S_C$ among the A-, B- and C-directions reach a maximum. Note that the A-, B- and C-directions are any directions that are orthogonal to each other.

[Calculation Unit 12]
The calculation unit 12 is configured to generate biomagnetic information on the basis of a signal detected by the magnetic sensor unit 11. For example, the calculation unit 12 includes an AD converter 12A configured to convert a periodic signal output from the magnetic sensor unit 11 into digital data, a recording unit 12B configured to temporarily record the digital data converted by the AD converter 12A and a control unit 12C configured to perform arithmetic processing on the digital data recorded in the recording unit 12B to generate the biomagnetic information.

The method of arithmetic processing performed by the calculation unit 12 using the control unit 12C is not particularly limited and may be averaging processing, moving average processing or Wiener filter processing. Averaging processing is preferred from the viewpoint of decreasing noise such as environmental magnetism.

[Wireless Module Unit 13]
The wireless module unit 13 is configured to wirelessly transmit the biomagnetic information generated by the calculation unit 12 from an antenna 18 to the external device. For example, the wireless module unit 13 includes a modulator configured to modulate the biomagnetic information generated by the calculation unit 12 into a radio wave signal, the antenna 18 configured to transmit the radio wave signal to the external device, and other components.

The above-described magnetic sensor unit 11 may include wiring for receiving signals and power supply. However, keep in mind that providing the magnetic sensor unit 11 with wiring for receiving external signals will increase preparation time due to the complexity of the wiring, or other such problems. Fast response is required when the muscle activity measurement device 1 is used for monitoring spinal cord and nerve function. Therefore, with the muscle activity measurement device 1 according to this embodiment, detection results by the magnetic sensor unit 11 are preferably transmitted to the external device using the wireless module unit 13.

[Power Supply Unit 14]

The power supply unit 14 is not particularly limited provided that the power supply unit 14 can supply electric power to the calculation unit 12 and the wireless module unit 13, and is preferably a small, lightweight battery such as a lithium battery.

[External Device]

Although not shown, the external device is made up of a receiver configured to receive data transmitted from the wireless module unit 13 of the muscle activity measurement device 1 via the antenna 18, an output unit configured to output the data received by the receiver to a display or a speaker, an operation unit formed of keys, buttons or a touch panel configured to process information input by a person conducting the measurement, a control unit configured to control each component of the muscle activity measurement device 1, a storage unit configured to accumulate received information and store a program for controlling the wireless module unit 13, and other components. With this configuration, the person conducting the measurement can operate the muscle activity measurement device 1 using the external device and can use the external device to obtain biomagnetic information from the muscle activity measurement device 1.

Incidentally, the above-described muscle activity measurement device 1 includes identification means for identifying a placement direction in which the device is placed on the body to be detected. The identification means includes identification information used for placing the muscle activity measurement device 1 with a sensing direction X of the magnetic sensor unit 11 substantially orthogonal to an extension direction of the muscle fibers in the body to be detected substantially. The identification means is not particularly limited to any form and may be, for example, identification information provided on a surface of a container 20 which stores the magnetic sensor unit 11. The identification information may be, for example, a display 24 in the installation direction of the muscle activity measurement device 1 on the front surface of the container 20.

Figure 3A:
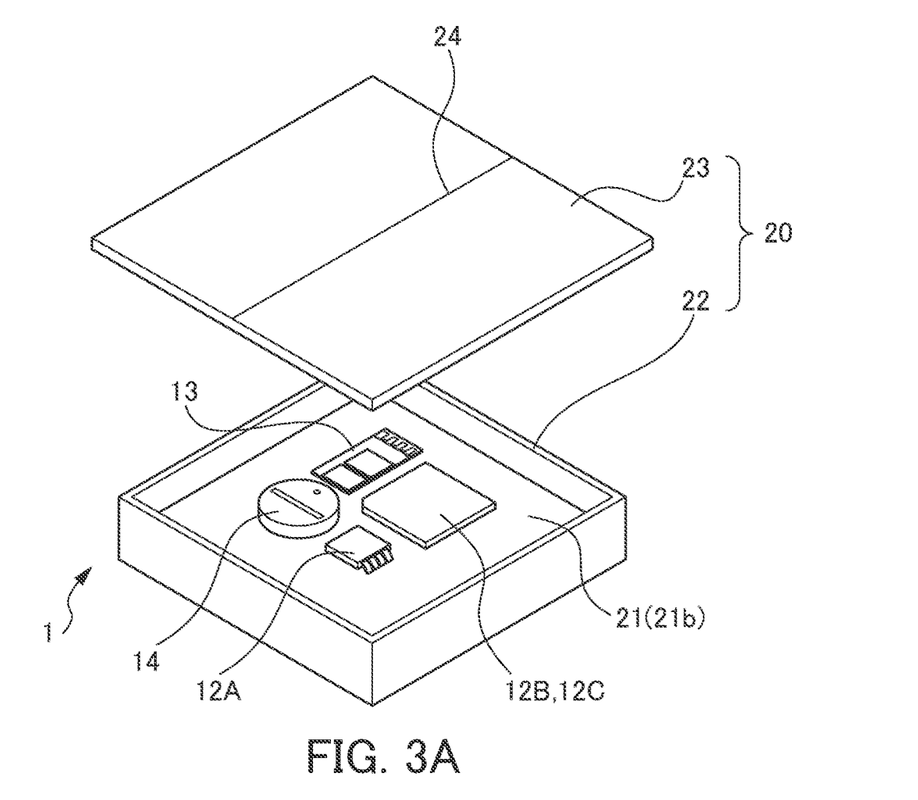
FIG. 3(a) is a perspective diagram for explaining a container in a state with an open lid plate.
Figure 3B:
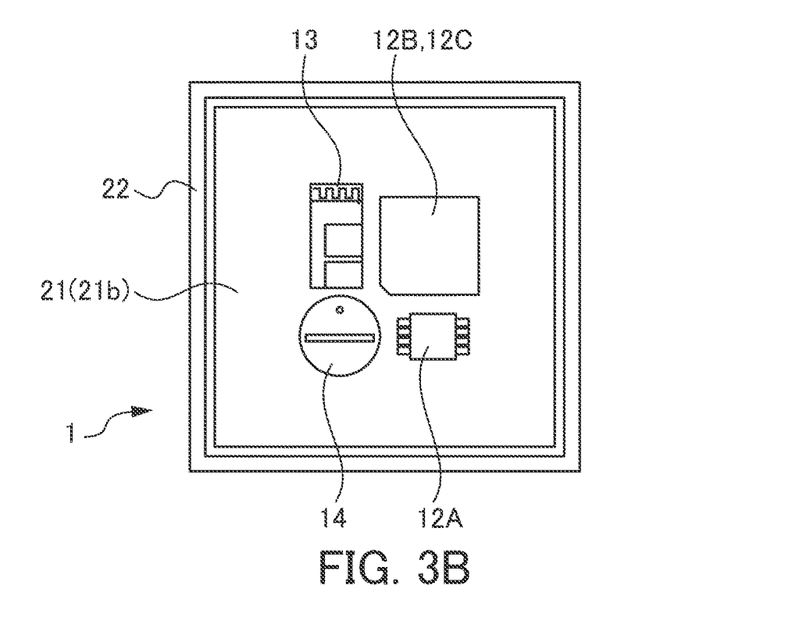
FIG. 3(b) is a plan view for explaining the state of a front surface of a substrate housed in the container.
Figure 4A:
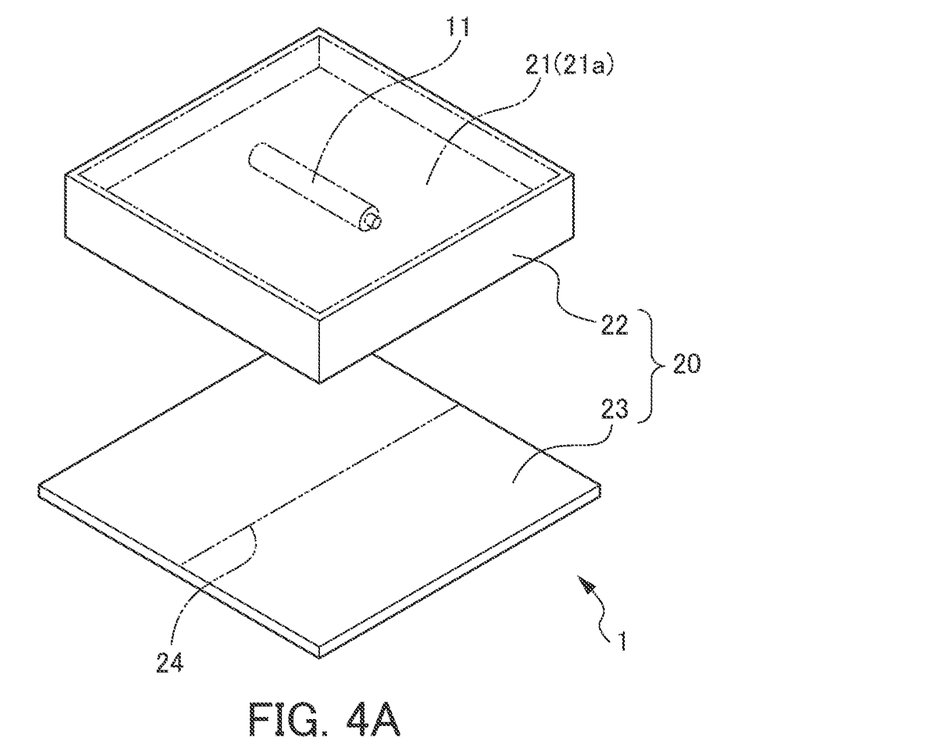
FIG. 4(a) is a perspective diagram for explaining a rear side of the container in a state with an open lid plate.
Figure 4B:
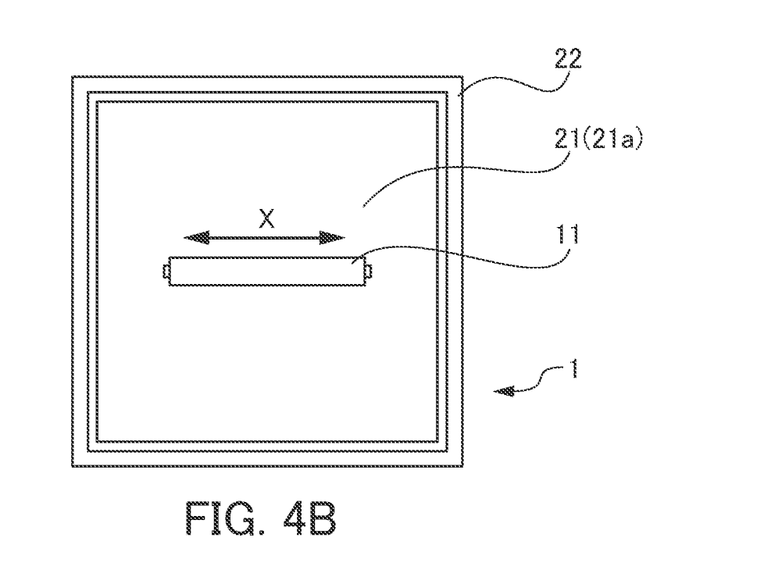
FIG. 4(b) is a bottom plan view for explaining the state of a rear surface of the substrate housed in the container.

Now, the configuration of the container 20 and the display 24 are described. FIG. 3 are diagrams for explaining the muscle activity measurement device according to the first embodiment when viewed from the front, in which FIG. 3(a) is a perspective diagram for explaining a container in a state with an open lid plate, and FIG. 3(b) is a plan view for explaining the state of a front surface of a substrate housed in the container. FIG. 4 are diagrams for explaining the muscle activity measurement device according to the first embodiment when viewed from the rear, in which FIG. 4(a) is a perspective diagram for explaining the rear side of the container in a state with an open lid plate, and FIG. 4(b) is a bottom plan view for explaining the state of a rear surface of the substrate housed in the container.

[Container 20]

As illustrated in FIGS. 3 and 4, the container 20 is formed of a container body (including a base plate) 22 which stores a substantially square substrate 21, and a substantially square lid plate 23 which covers an opening in the container body 22. The shape of the container 20 is not particularly limited and may be a shape other than a square, such as a rectangle or an ellipse. Herein, the shape of the container 20 refers to the shape of the opening in the container body 22, that is the shape of the lid plate 23. The first embodiment deals with a case where the shape of the opening in the container 20, that is the shape of the lid plate 23 is a substantially square shape.

The container 20 also houses the magnetic sensor unit 11, the calculation unit 12 (AD converter 12A, recording unit 12B and control unit 12C), the wireless module unit 13 and the power supply unit 14. The magnetic sensor unit 11 is preferably installed on a rear surface 21a of the substrate 21 which opposes the body via the container body 22 to facilitate easy detection of magnetism in the body to be detected. The longitudinal direction of the magnetic sensor unit 11 to be installed is the sensing direction X. The calculation unit 12 (AD converter 12A, recording unit 12B and control unit 12C), the wireless module unit 13 and the power supply unit 14 are preferably mounted to a front surface 21b of the substrate 21. The calculation unit 12 (AD converter 12A, recording unit 12B and control unit 12C), the wireless module unit 13 and the power supply unit 14 may generate a small amount of magnetic noise such as electromagnetic waves. In order to deal with this, the substrate 21 which can block magnetism may be provided if the effect of magnetic noise from outside the detection direction is large. While the container body 22 may not include a base plate, a base pate is preferably included to improve strength of the container body 22.

Note that the calculation unit 12 (AD converter 12A, recording unit 12B and control unit 12C), the wireless module unit 13 and the power supply unit 14 may be disposed on the same surface as the magnetic sensor unit 11 and magnetic noise from the calculation unit 12 (AD converter 12A, recording unit 12B and control unit 12C), the wireless module unit 13 and the power supply unit 14 may be prevented from reaching the magnetic sensor unit 11. However, in terms of reducing the size of the muscle activity measurement device 1, these components are preferably disposed on the front and rear surfaces of the substrate 21 as described above. The positions at which the magnetic sensor unit 11, the calculation unit 12 (AD converter 12A, recording unit 12B and control unit 12C), the wireless module unit 13 and the power supply unit 14 are disposed on the substrate 21 are not particularly limited, but the center of gravity of the muscle activity measurement device 1 is preferably taken into account in consideration of stability when placing the device on the body.

The material of the substrate 21 is preferably a material which can block environmental magnetism so that magnetic noise generated by the calculation unit 12, the wireless module unit 13 and the power supply unit 14 does not affect the muscular magnetic field. Examples of such a material include permalloy, ferrite, sendust or a Co-based amorphous material.

The material of the container body 22 is not particularly limited, provided that the container body 22 blocks the magnetic field generated as a result of muscle activity in the body. Examples of preferable materials include polyetheretherketone (PEEK) and polyethylene terephthalate (PET) resin.

[Display 24]

As illustrated in FIG. 3, the display 24 is disposed on the lid plate 23 of the container 20 and is a display line which extends in a direction substantially orthogonal to the sensing direction X of the magnetic sensor unit 11 housed in the container body 22. The form of the display 24 is not particularly limited provided that the person conducting the measurement can identify the display. For example, the display 24 may be a linear symbol attached to the lid plate 23, a linear protrusion, text information, or a combination thereof. In addition, the display 24 may be a component provided with a seal member printed with a symbol or text information.

Because the muscle activity measurement device 1 includes the display 24, the person conducting the measurement can easily identify the placement direction of the muscle activity measurement device 1 (container 20). As a result, the muscle activity measurement device 1 can more accurately measure muscle activity to be detected.

[Muscle Activity Measurement Method]

A muscle activity measurement method according to this embodiment is a method of disposing the muscle activity measurement device 1 on the body surface of a body 100 with the sensing direction X of the magnetic sensor unit 11 substantially orthogonal to the extending direction of muscle fibers in the body 100 to be detected.

Figure 5:
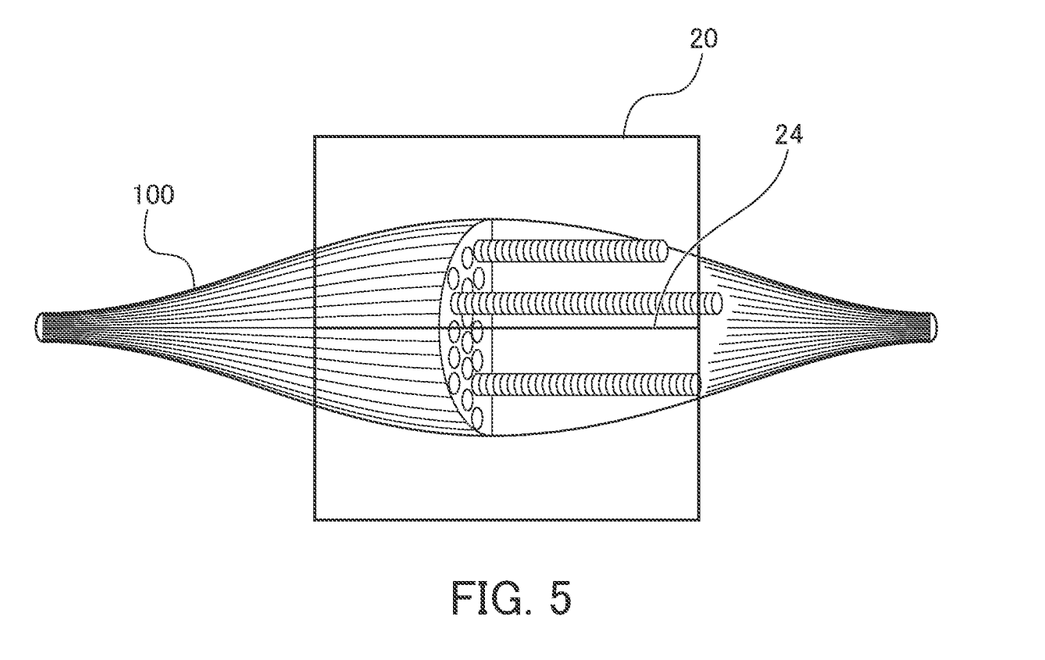
FIG. 5 is a schematic diagram for explaining a muscle activity measurement method according to the first embodiment.

FIG. 5 is a schematic diagram for explaining a muscle activity measurement method according to the first embodiment. As illustrated in FIG. 5, the display 24 is attached to the container 20 in a direction orthogonal to the sensing direction X of the magnetic sensor unit 11. The container 20 is disposed such that the person conducting the measurement can easily identify the placement direction using the display 24 when the muscle activity measurement device 1 (container 20) is placed on the body surface of the body 100 and the display 24 of the container 20 substantially coincides with the extension direction of the muscle fibers. As a result, the muscle activity measurement device 1 (container 20) can detect muscular magnetic field with high sensitivity because the muscle activity measurement device 1 (container 20) is disposed such that the sensing direction X of the magnetic sensor unit 11 is substantially orthogonal to the extension direction of the muscle fibers in the body 100.

Second Embodiment

[Muscle Activity Measurement Device 1']

Figure 6A:
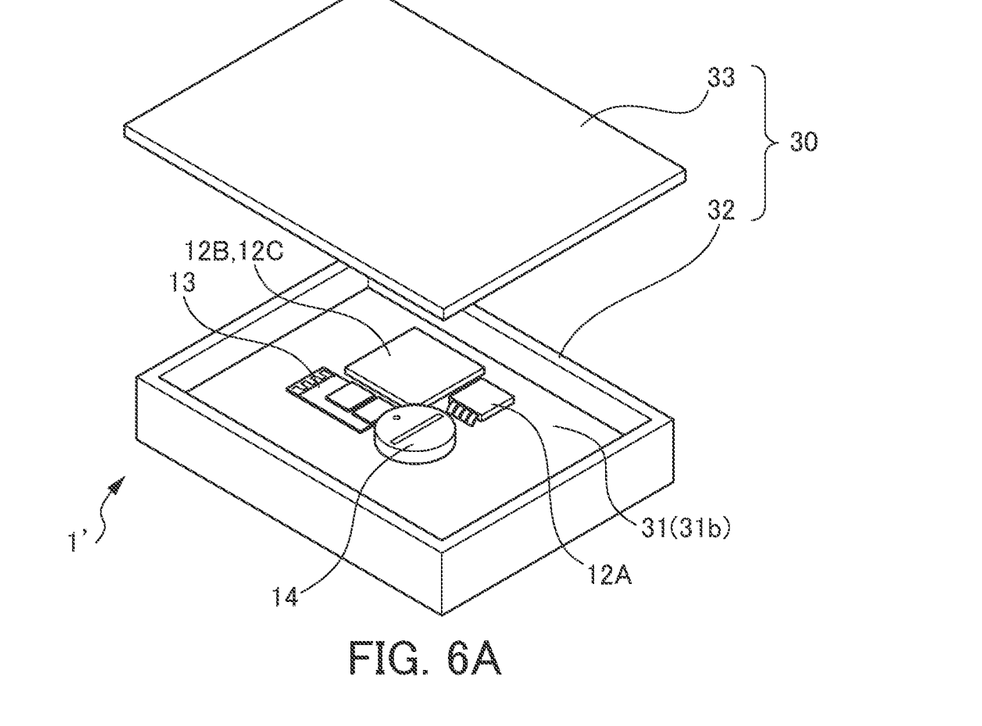
FIG. 6(a) is a perspective diagram for explaining a container in a state with an open lid plate.
Figure 6B:
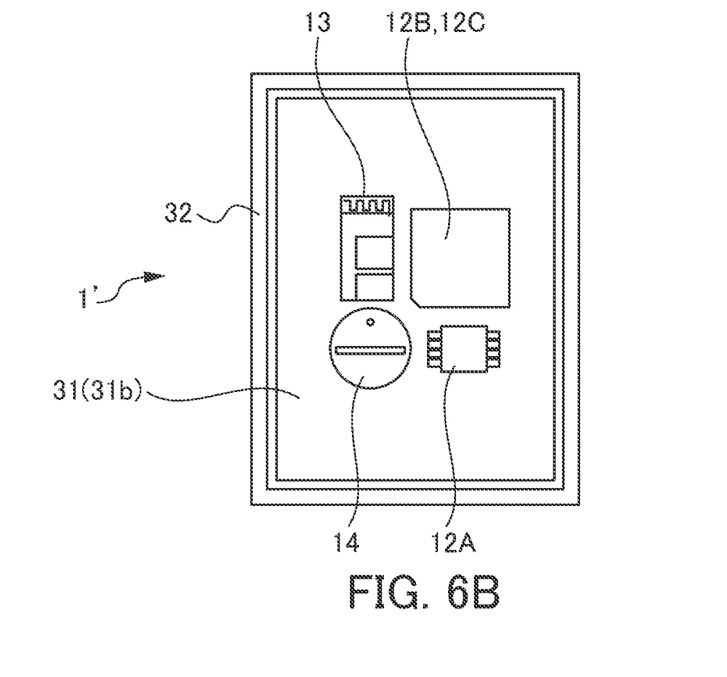
FIG. 6(b) is a plan view for explaining the state of a front surface of a substrate housed in the container.
Figure 7A:
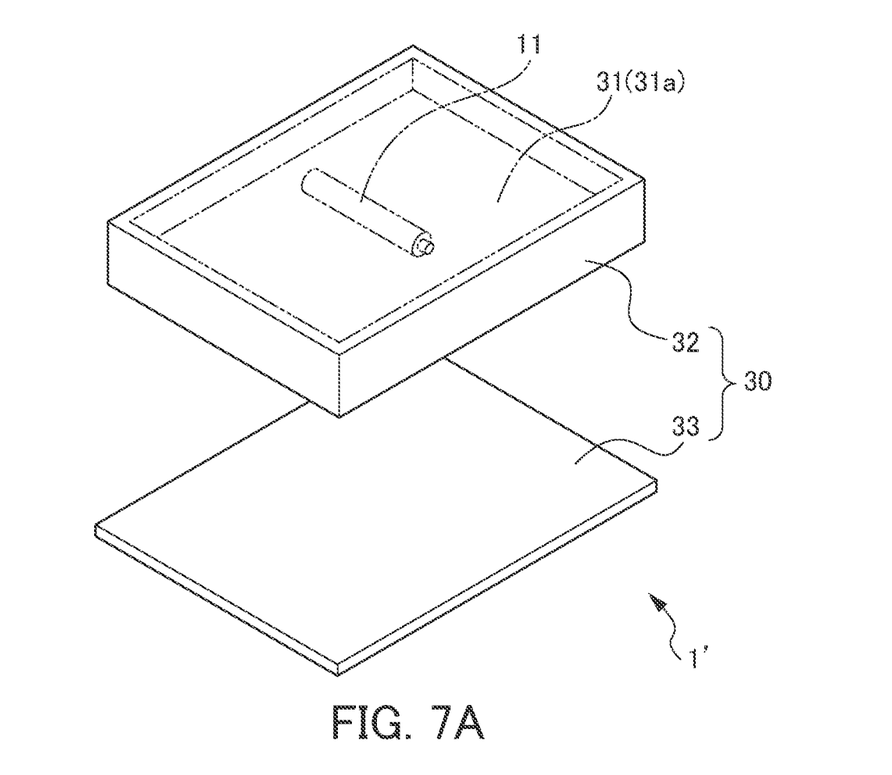
FIG. 7(a) is a perspective diagram for explaining the rear side of the container in a state with an open lid plate.
Figure 7B:
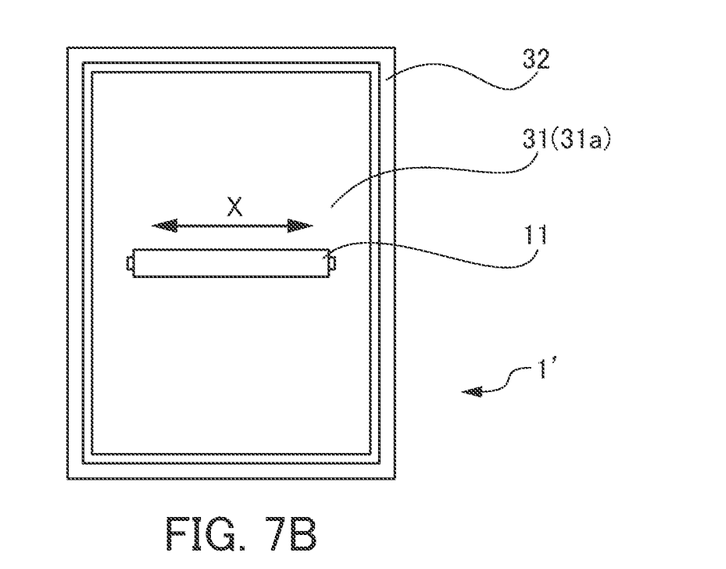
FIG. 7(b) is a bottom plan view for explaining the state of a rear surface of the substrate housed in the container.

A muscle activity measurement device 1' according to a second embodiment has the same configuration as the muscle activity measurement device 1 according to the first embodiment except for identification means for identifying the placement position of the muscle activity measurement device 1'. FIG. 6 are diagrams for explaining a muscle activity measurement device according to a second embodiment of the present invention when viewed from the front, in which FIG. 6(*a*) is a perspective diagram for explaining a container in a state with an open lid plate, and FIG. 6(*b*) is a plan view for explaining the state of a front surface of a substrate housed in the container. FIG. 7 are diagrams for explaining the muscle activity measurement device according to the second embodiment when viewed from the rear, in which FIG. 7(*a*) is a perspective diagram for explaining the rear side of the container in a state with an open lid plate, and FIG. 7(*b*) is a bottom plan view for explaining the state of a rear surface of the substrate housed in the container. In FIGS. 6 and 7, components that are the same as those described above are denoted by the same reference symbols and descriptions thereof are omitted.

The configuration of a container 30, which is a characteristic component of the muscle activity measurement device 1' according to this embodiment, is described below. As illustrated in FIGS. 6 and 7, the container 30 is formed of a container body (including a base plate) 32 which houses a substantially rectangular substrate 31, and a substantially rectangular lid plate 33 which covers an opening in the container body 32.

As described above, the container 30 houses the magnetic sensor unit 11, the calculation unit 12 (AD converter 12A, recording unit 12B and control unit 12C), the wireless module unit 13 and the power supply unit 14. The magnetic sensor unit 11 is preferably placed on a rear surface 31*a* of the substrate 31 which opposes the body via the container body 32 to facilitate easy detection of magnetism in the body to be detected. The longitudinal direction of the magnetic sensor unit 11 to be placed is the sensing direction X. The calculation unit 12 (AD converter 12A, recording unit 12B and control unit 12C), the wireless module unit 13 and the power supply unit 14 are preferably mounted on the rear surface 31*a* of the substrate 31. The calculation unit 12 (AD converter 12A, recording unit 12B and control unit 12C), the wireless module unit 13 and the power supply unit 14 may generate a small amount of magnetic noise such as electromagnetic waves. In order to deal with this, the substrate 31, which can block magnetism, is preferably disposed between the magnetic sensor unit 11 and the calculation unit 12, wireless module unit 13 and power supply unit 14 such that magnetic noise from outside the detection direction does not affect the muscular magnetic field. The positions at which the magnetic sensor unit 11, the calculation unit 12 (AD converter 12A, recording unit 12B and control unit 12C), the wireless module unit 13 and the power supply unit 14 are disposed on the substrate 31 are not particularly limited, but stability when placing the device on the body is preferably taken into account.

In the muscle activity measurement device 1' according to this embodiment, the shape of the container 30 is the identification means. Because the shape of the container 30 is a rectangular shape with a longitudinal direction and a transverse direction, the person conducting the measurement can easily place the container 30 such that the longitudinal direction of the container 30 substantially coincides with the extension direction of the muscle fibers in the body to be detected. As a result, in the muscle activity measurement device 1' (container 30), the transverse direction of the container 30 and the sensing direction X of the magnetic sensor unit 11 substantially coincide with each other, and the sensing direction X of the magnetic sensor unit 11 is substantially orthogonal to the extension direction of the muscle fibers of the body 100. Because of this, muscle activity to be detected can be measured more accurately.

<Muscle Activity Measurement Method According to Second Embodiment>

A muscle activity measurement method according to this embodiment is a method of disposing the muscle activity measurement device 1' on the body surface of the body 100 with the sensing direction X of the magnetic sensor unit 11 substantially orthogonal to the extending direction of muscle fibers in the body 100 to be detected.

Figure 8:
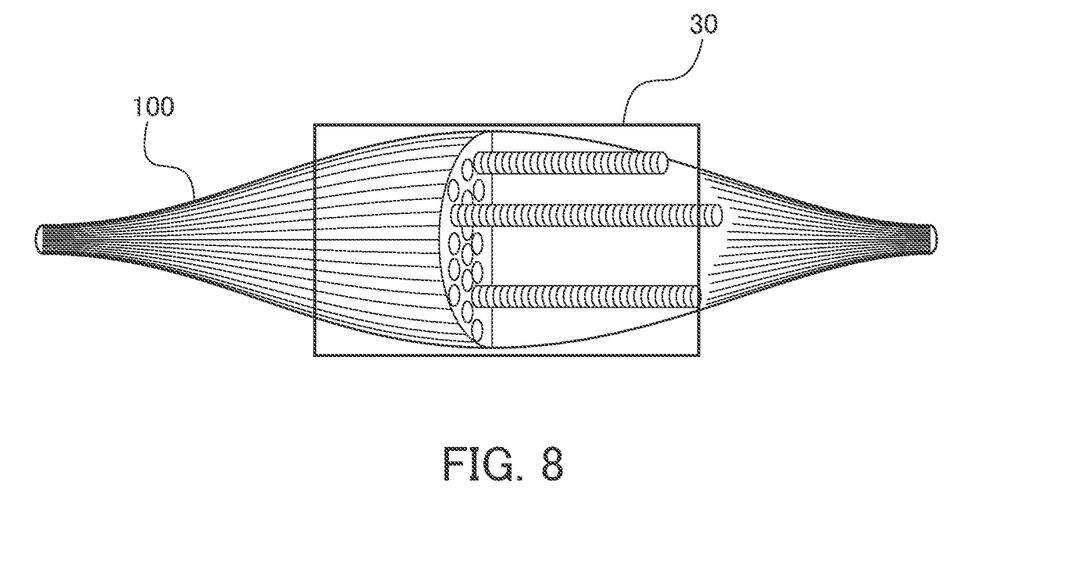
FIG. 8 is a schematic diagram for explaining a muscle activity measurement method according to the second embodiment.

FIG. 8 is a schematic diagram for explaining the muscle activity measurement method according to the second embodiment. As illustrated in FIG. 8, the container 30 is formed into a rectangular shape with a longitudinal direction and a transverse direction, and the transverse direction substantially coincides with the sensing direction X of the magnetic sensor unit 11. The person conducting the measurement can easily identify the placement direction on the basis of the shape of the container 30 when placing the muscle activity measurement device 1' (container 30) on the body surface of the body 100. In other words, the device is guided such that the longitudinal direction of the container 30 substantially coincides with the extension direction of the muscle fibers in the body 100. As a result, the muscle activity measurement device 1' (container 30) can detect the muscular magnetic field with high sensitivity because the muscle activity measurement device 1' (container 30) is disposed such that the sensing direction X of the magnetic sensor unit 11 is substantially orthogonal to the extension direction of the muscle fibers in the body 100.

Note that with the muscle activity measurement devices and the muscle activity measurement methods according to the first and second embodiments, as illustrated in FIGS. 5 and 8, there has been described a case in which the subject of detection is the muscle fibers in the body and the identification means includes identification information used for placing the muscle activity measurement device 1 with the sensing direction X of the magnetic sensor unit 11 substantially orthogonal to the extension direction of the muscle fibers in the body to be detected. However, the identification means is not limited thereto, and the subject to be detected by the muscle activity measurement device according to this embodiment may be muscle cells generated by the muscular magnetic field due to muscular activity in the body. For example, the subject of detection may something other than muscle fiber (skeletal muscles) such as the myocardium or smooth muscles.

In other words, the identification means of the muscle activity measurement device according to this embodiment may include identification information used for placing the muscle activity measurement device such that the sensing direction X of the magnetic sensor unit 11 and a direction of the muscular magnetic field of muscle fibers (skeletal muscles) or muscle activity of the myocardium or smooth muscles in the body to be detected substantially coincide.

EXAMPLES

Example 1

Figure 9A:
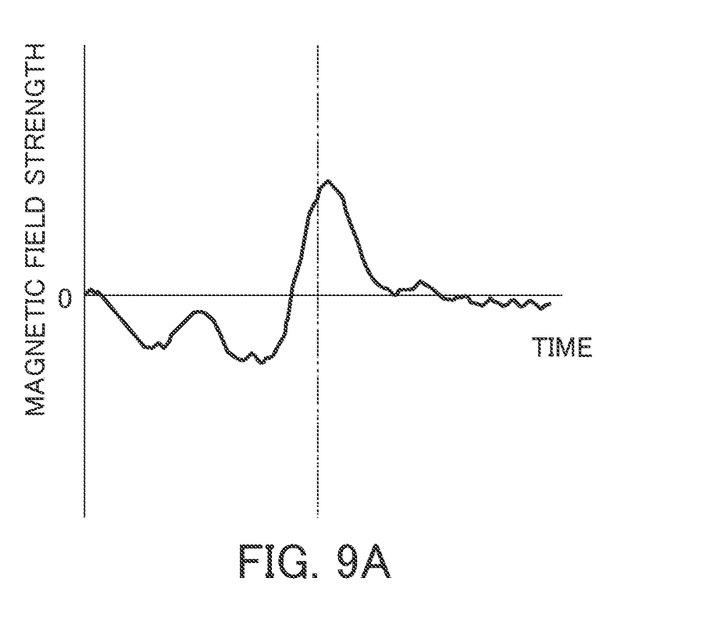
FIG. 9(a) is a waveform chart showing waveforms obtained from a magnetic sensor unit in Example 1.

As described in the first embodiment, the muscle activity measurement device 1 was placed on the thenar eminence (see FIG. 5) such that the display 24 of the container 20 substantially coincided with the extension direction of muscle fibers, that is, such that the sensing direction X of the magnetic sensor unit 11 was substantially orthogonal to the extension direction of muscle fibers. With this configuration, the sensing direction X of the magnetic sensor unit 11 and the extension direction of muscle fibers were substantially orthogonal to each other. Then, muscular magnetic field was measured by electrically stimulating the median nerve with the wrist. Results of the measurement are shown in FIG. 9(*a*). In FIG. 9(*a*), the point 0 represents the timing at which electrical stimulation was applied, and the two-dot chain line represents the timing at which the muscular magnetic field was generated.

Comparative Example 1

Figure 9B:
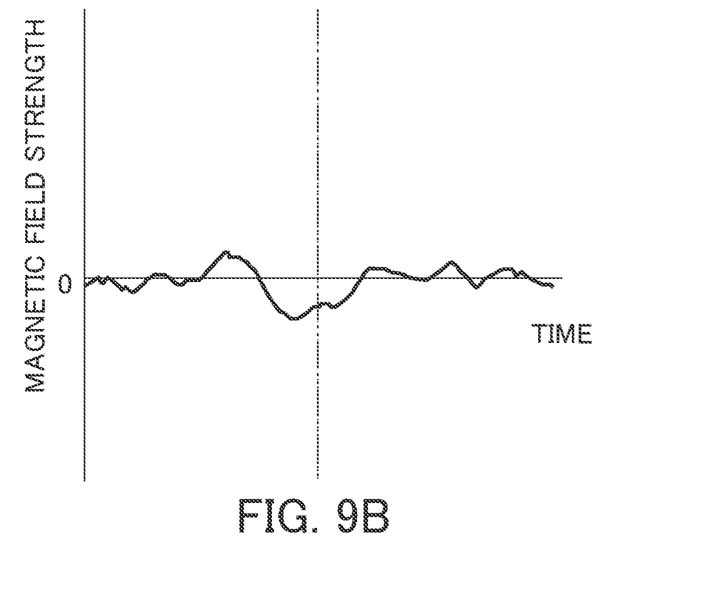
FIG. 9(b) is a waveform chart showing waveforms obtained from a magnetic sensor unit in Comparative Example 1.

The muscle activity measurement device 1 was placed on the thenar eminence such that the display 24 of the container 20 was orthogonal to the extension direction of muscle fibers, that is, such that the sensing direction X of the magnetic sensor unit 11 substantially coincided with the extension direction of muscle fibers. With this configuration, the sensing direction X of the magnetic sensor unit 11 and the extension direction of muscle fibers substantially coincided. Then, muscular magnetic field was measured by electrically stimulating the median nerve with the wrist. Results of the measurement are shown in FIG. 9(*b*). In FIG. 9(*b*), the point 0 represents the timing at which electrical stimulation was applied, and the two-dot chain line represents the timing at which the muscular magnetic field was generated.

[Considerations]

From the results shown in FIGS. 9(*a*) and 9(*b*), it was confirmed that in Example 1 in which the muscle activity measurement device 1 was placed such that the sensing direction X of the magnetic sensor unit 11 was substantially orthogonal to the extension direction of muscle fibers, the muscle measurement device 1 exhibited higher sensitivity than in Comparative Example 1 in which the muscle activity measurement device 1 was disposed such that the sensing direction X of the magnetic sensor unit 11 substantially coincided with the extension direction of muscle fibers. As a result, it was confirmed that the muscle activity measurement device 1 can more accurately measure muscle activity when disposed such that the sensing direction X of the magnetic sensor unit 11 is substantially orthogonal to the extension direction of muscle fibers.

Note that while the muscle activity measurement devices 1 and 1' according to the embodiments can be preferably applied to an intraoperative spinal cord and nerve function monitoring device, it goes without saying that the present invention is not limited thereto. For example, the muscle activity measurement device according to the present invention may be applied to a diagnostic device used for diagnosing diseases that affect muscles, such as polymyositis, muscle dystrophy and myasthenia gravis, or diseases that affect nerves, such as peripheral neuritis, diabetic neuropathy, compressive spinal cord injury, spinal radiculopathy and amyotrophic lateral sclerosis.

Further, in the present invention, it is clear that there is strong linearity and correlation between the amplitude of magnetic field fluctuation measured by the muscle activity measurement device and the amount of movement of patient muscle activity. Because of this, it is also possible to measure the movement amount of the subject on the basis of the amplitude of magnetic field fluctuation. In addition, according to the present invention, it is clear that there is strong linearity and correlation between the inclination of magnetic field fluctuation measured by the muscle activity measurement device and movement speed of patient muscle activity. Because of this, it is also possible to measure the movement speed of the subject on the basis of the inclination of magnetic field fluctuation. Further, the muscle activity measurement device according to the present invention can also measure slight magnetic field fluctuation due to the physical contraction and expansion of blood vessels and measure the heart rate of the patient. Therefore, the muscle activity measurement device according to the present invention may be applied to a measurement device configured to measure muscle activity of a patient, motor function of a patient, muscle fatigue of a patient and heart rate of a patient. For example, the present invention may be applied to training purposes for athletes. In particular, while measurement devices that have electrodes cannot be used underwater for measuring swimmers, a measurement device using a magnetic sensor such as that described above can be used. Further, if the muscle activity measurement device includes a wireless module unit in addition to the magnetic sensor unit, complex wires can be eliminated and user-friendliness can be improved.

Because the muscle activity measurement device according to the present invention can instantaneously measure magnetic field fluctuations, movement amount and speed of muscle activity can also be instantaneously measured on the basis of the magnetic field fluctuations measured by the muscle activity measurement device. Therefore, the muscle activity measurement device according to the present invention can be applied to an intention detection device configured to instantaneously determine a response (Yes or No) to a question from the patient on the basis of the movement amount and speed of muscle activity. For example, the muscle activity measurement device can detect muscle activity of the frontalis muscle which raises and lowers the eyebrows, to thereby detect the intention of the patient.

If the muscle activity measurement device according to the present invention is used to measure muscle activity of a patient, motor function of a patient, muscle fatigue of a patient and heart rate of a patient, or detect intention, the container is preferably formed into a shape that can be worn by the patient. In this case, the identification means may be a display on the front surface of the container or may be the shape of the container in which the mounting direction is set to a predetermined direction. For example, the container may be made of a flexible material formed into a strip to be wrapped around an upper arm (bicep) or femur (quadriceps). In addition, if the muscle activity measurement device includes a wireless module unit in addition to the magnetic sensor unit in the container, complex wires can be eliminated and user-friendliness can be improved.

In addition, the muscle activity measurement device according to the present invention may be mounted to a device used to support movement of the wearer by being worn on the body for the fields of rehabilitation or health support. For example, the muscle activity measurement device may be mounted to a motor function improvement device for determining a support operation to supplement the function of muscle activity and drive a power unit on the basis of biomagnetic information obtained by the muscle activity measurement device.

EXPLANATION OF REFERENCE NUMERALS 1, 1' muscle activity measurement device
11 magnetic sensor unit
12 calculation unit
12A AD converter
12B recording unit
12C control unit
13 wireless module unit
14 power supply unit
18 antenna
20, 30 container
21, 31 substrate
22, 32 container body
23, 33 lid plate
24 display

The invention claimed is:

1. A muscle activity measurement device comprising:
a magnetic sensor unit configured to detect a magnetic field generated from a body;
a container;
identification information to identify a placement direction of the muscle activity measurement device and used for placing the muscle activity measurement device such that a sensing direction of the magnetic sensor unit is substantially orthogonal to an extension direction of muscle fibers in the body to be detected;
a calculation unit configured to generate biomagnetic information on the basis of a signal detected by the magnetic sensor unit;
a wireless module configured to wirelessly transmit the biomagnetic information generated by the calculation unit to an external device; and
a power supply unit configured to supply electric power to the magnetic sensor unit, the calculation unit, and the wireless module,
wherein the container comprises:
a container body that comprises a substrate having a front surface and a rear surface and has an opening on a front surface side of the substrate, and
a lid plate that covers the opening of the container body and has an inner surface facing the front surface of the substrate and an outer surface,
wherein the identification information comprises at least one data selected from the group consisting of a display of the placement direction of the muscle activity measurement device on the front surface of the container and a shape of the container, and
wherein the magnetic sensor unit is provided on the rear surface of the substrate of the container, the calculation unit and the wireless module are mounted to the front surface of the substrate, and the identification information is provided on the outer surface of the lid plate of the container.

2. A muscle activity measurement device comprising:
a magnetic sensor unit configured to detect a magnetic field generated from a body;
a container;
identification information to identify a placement direction of the muscle activity measurement device and used for placing the muscle activity measurement device such that a sensing direction of the magnetic sensor unit substantially coincides with a direction of a muscular magnetic field generated due to muscle activity in the body to be detected;
a calculation unit configured to generate biomagnetic information on the basis of a signal detected by the magnetic sensor unit;
a wireless module configured to wirelessly transmit the biomagnetic information generated by the calculation unit to an external device; and
a power supply unit configured to supply electric power to the magnetic sensor unit, the calculation unit and the wireless module,
wherein the container comprises:
a container body that comprises a substrate having a front surface and a rear surface and has an opening on a front surface side of the substrate, and
a lid plate that covers the opening of the container body and has an inner surface facing the front surface of the substrate and an outer surface,
wherein the identification information comprises at least one data selected from the group consisting of a display of the placement direction of the muscle activity measurement device on the front surface of the container and a shape of the container, and
wherein the magnetic sensor unit is provided on the rear surface of the substrate of the container, the calculation unit and the wireless module are mounted to the front surface of the substrate, and the identification information is provided on the outer surface of the lid plate of the container.

3. The muscle activity measurement device according to claim 1, wherein the container has a rectangular shape or an elliptical shape.

4. The muscle activity measurement device according to claim 3, wherein a transverse direction of the container substantially coincides with a sensing direction of the magnetic sensor unit.

5. A muscle activity measurement method of disposing the muscle activity measurement device of claim 1 on a body surface of the body with a sensing direction of the magnetic sensor unit substantially orthogonal to an extension direction of muscle fibers in the body to be detected.

6. A method of using a muscle activity measurement device, comprising:
provide a muscle activity measurement device comprising a magnetic sensor unit configured to detect a magnetic field generated from a body, a container, identification information provided to identify a placement direction of the muscle activity measurement device, a calculation unit configured to generate biomagnetic information on the basis of a signal detected by the magnetic sensor unit, a wireless module configured to wireles transmit the biomagnetic information generated by the calculation unit to an external device, and a power supply unit configured to supply electric power to the magnetic sensor unit, the calculation unit and the wireless module,
wherein the container comprises a container body that comprises a substrate having a front surface and a rear surface and has an opening on a front surface side of the substrate and a lid plate that covers the opening of the container body and has an inner surface facing the front surface of the substrate and an outer surface,
wherein the magnetic sensor unit being provided on the rear surface of the substrate of the container,
wherein the calculation unit and the wireless module being mounted to the front surface of the substrate, the identification information comprises at least one data selected from the group consisting of a display of the placement direction of the muscle activity measurement device on the front surface of the container and a shape of the container, and
wherein the identification information being provided on the outer surface of the lid plate of the container; and
placing, based on the identification information, the muscle activity measurement device such that a sensing direction of the magnetic sensor unit is substantially orthogonal to an extension direction of muscle fibers in the body to be detected.

7. A method of using a muscle activity measurement device, comprising:
providing a muscle activity measurement device comprising a magnetic sensor unit configured to detect a magnetic field generated from a body, a container, identification information provided to identify a placement direction of the muscle activity measurement device, a calculation unit configured to generate biomagnetic information on the basis of a signal detected by the magnetic sensor unit, a wireless module configured to wirelessly transmit the biomagnetic information generated by the calculation unit to an external device, and a power supply unit configured to supply electric power to the magnetic sensor unit, the calculation unit and the wireless module,
wherein the container comprises a container body that comprises a substrate having a front surface and a rear surface and has an opening on a front surface side of the substrate, and a lid plate that covers the opening of the container body and has an inner surface facing the front surface of the substrate and an outer surface,
wherein the magnetic sensor unit being provided on the rear surface of the substrate of the container,
wherein the calculation unit and the wireless module being mounted to the front surface of the substrate, the identification information comprises at least one data selected from the group consisting of a display of the placement direction of the muscle activity measurement device on the front surface of the container and a shape of the container,
wherein the identification information being provided on the outer surface of the lid plate of the container; and
placing, based on the identification information, the muscle activity measurement device such that a sensing direction of the magnetic sensor unit coincides with a direction of a muscular magnetic field generated due to muscle activity in the body to be detected.

* * * * *